United States Patent

Shin et al.

(10) Patent No.: US 7,446,165 B2
(45) Date of Patent: Nov. 4, 2008

(54) BENZIMIDAZOLE COMPOUND

(75) Inventors: Chong-kyu Shin, Daejeon (KR); Young-ji Tae, Seoul (KR); Bong-keun Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 236 days.

(21) Appl. No.: 11/200,237

(22) Filed: Aug. 10, 2005

(65) Prior Publication Data

US 2006/0036061 A1 Feb. 16, 2006

(30) Foreign Application Priority Data

Aug. 11, 2004 (KR) .................. 10-2004-0063229

(51) Int. Cl.
*C07D 235/04* (2006.01)
*C07D 235/10* (2006.01)
*C07D 235/20* (2006.01)

(52) U.S. Cl. .............. 528/423; 548/301.7; 548/302.7; 548/354.1; 548/343.5; 548/300.1

(58) Field of Classification Search .............. 528/183; 424/59
See application file for complete search history.

(56) References Cited

U.S. PATENT DOCUMENTS

| 5,317,078 A | 5/1994 | Connell et al. |
| 5,412,059 A | 5/1995 | Connell et al. |
| 5,525,436 A | 6/1996 | Savinell et al. |
| 5,824,698 A | 10/1998 | Hasler et al. |
| 2003/0152532 A1* | 8/2003 | Candau ............. 424/59 |

FOREIGN PATENT DOCUMENTS

SU 879985 3/1986

OTHER PUBLICATIONS

Gavrilov et al Spectral study . . . , Izvestiya VUZ, FizikaN2p. 119-121, (1970).*
Coville, et al. "Oxidative Cyclodehydrogenation of Aromatic Bis (o-aminoanils)"; J. Org. Chem., vol. 42, No. 22, 1977.
Kim, et al. "Synthesis of Poly (2, 5-benzimidazole) for Use as a Fuel-Cell Membrane)"; Macromol. Rapid Communication, 2004.

* cited by examiner

*Primary Examiner*—Rabon Sergent
*Assistant Examiner*—Gregory Listvoyb
(74) *Attorney, Agent, or Firm*—McKenna Long & Aldridge LLP

(57) ABSTRACT

The present invention relates to a novel benzimidazole compound represented by formula 1. The novel benzimidazole compound of the present invention is very useful for the production of polymers used as a functional polymer thin film by polymerization with bishydroxy compound.

[Formula 1]

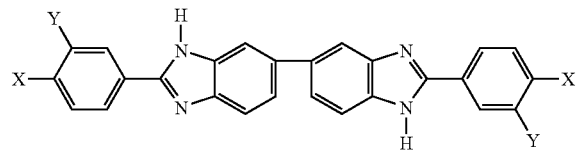

Wherein,
X is a halogen such as F, Cl, Br or I,
Y is a functional group having strong electron-drawing force such as nitro ($—NO_2$) or trifluoromethyl ($—CF_3$).

4 Claims, No Drawings

BENZIMIDAZOLE COMPOUND

This application claims priority to Korean Application No. 10-2004-0063229, filed Aug. 11, 2004 and which is hereby incorporated by reference in its entirety.

TECHNICAL FIELD

The present invention relates to a novel benzimidazole compound, more precisely, a benzimidalzole compound available for the production of a polymer for functional polymer thin film by polymerization with bishydroxy compound.

BACKGROUND ART

Polybenzimidazole (PBI) has been widely used owing to its excellent mechanical and physical characteristics, and in particular, used for the production of fire wall or fire coat owing to its strong heat resistance.

In regard to polybenzimidazole, the structure of polybenzimidazole in which two benzimidazole compounds are directly bound each other and phenyl group not substituted with halogen is bound at No. 2 site is described in Russian (Soviet Union) patent No. 879985 and J. Org. Chem. 1977, 42(22); p 3485~91.

The structures having substitution of halogen, hydroxy, cyano, alkoxy, or alkyl are described in U.S. Pat. No. 5,824,698, and the structure having substitution of phenyl with hydroxy is described in U.S. Pat. Nos. 5,317,078 and 5,412,059.

According to the description of U.S. Pat. No. 5,525,436, polybenzimizole thin film doped with phosphoric acid shows excellent proton conductivity at high temperature over 100° C., which directs the recent studies to the use of polybenzimidazole as an electrolyte for fuel cell at high temperature.

However, the production of polymer thin film is not easy because the isolation of polymerized polybenzimidazole from a reaction solution is very difficult owing to its low solubility in a solvent (H. -J. Kim et al., *Macromol. Rapid Commun.*, 25, 894 (2004)).

DISCLOSURE OF THE INVENTION

It is an object of the present invention to provide a novel benzimidazole compound having a completely different structure from that of the conventional benzimidazole compounds.

In order to achieve the above object of the present invention, the invention provides a benzimidazole compound represented by the following formula 1.

Wherein,

X is a halogen such as F, Cl, Br or I, Y is a functional group having strong electron-drawing force such as nitro (—NO$_2$) or trifluoromethyl (—CF$_3$).

In the formula 1, X is preferred to be F or Cl and Y is preferred to be trifluoromethyl or nitro.

The present invention also provides a benzimidazole polymer synthesized by using the benzimidazole compound of formula 1 as a monomer.

The present invention further provides a functional polymer thin film containing the synthesized benzimidazole polymer.

The functional polymer thin film is preferred to be doped with phosphoric acid or sulfuric acid, and can be used as an electrolyte of fuel cell.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 3.756 g (10.430 mmol) of 3,3'-diaminobenzidine tetrahydrochloride dehydrate and 4.430 g (20.854 mmol) of 4-fluoro-3-(trifluoromethyl) benzoic acid were dissolved in 50 ml of PPMA(phosphorous pentoxide/methansulfonic acid), followed by reaction at 130° C. for 5 hours. The reaction solution was poured in 1 M of sodium hydroxide. The precipitate was filtered and the filtrate was washed with hot distilled water several times. The filtrate was dried at 100° C. in a vacuum oven for over 12 hours, followed by recrystalization with ethanol, resulting in 5.05 g of pure benzimidazole (2,2'-bis(4-fluoro-3-(trifluoromethyl)) -5,5'-bibenzimidazole). The reaction formula is shown below. The chemical structure of the obtained benzimidazole was confirmed by $^1$H-NMR.

$^1$H-NMR(DMSO-d$_6$): 8.18-8.07(m, 2H), 7.45(d, 1H), 7.35-7.23(m, 2H), 7.19-7.12(m, 1H)

[Formula 1]

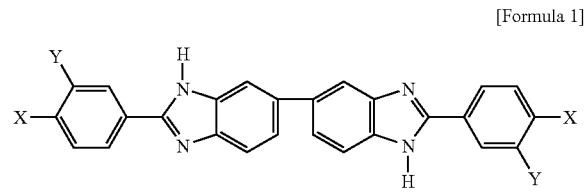

[Reaction Formula 1]

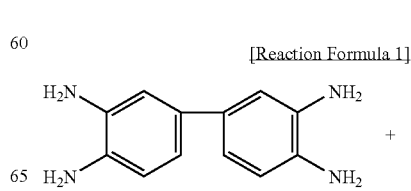

-continued

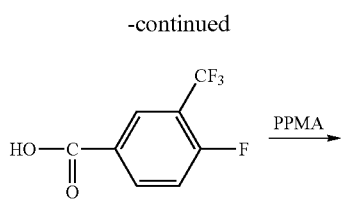

INDUSTRIAL APPLICABILITY

As explained hereinbefore, the novel benzimidazole compound of the present invention is very useful for the production of polymers used as a functional polymer thin film by polymerization with bishydroxy compound.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A benzimidazole compound represented by the following formula 1,

[Formula 1]

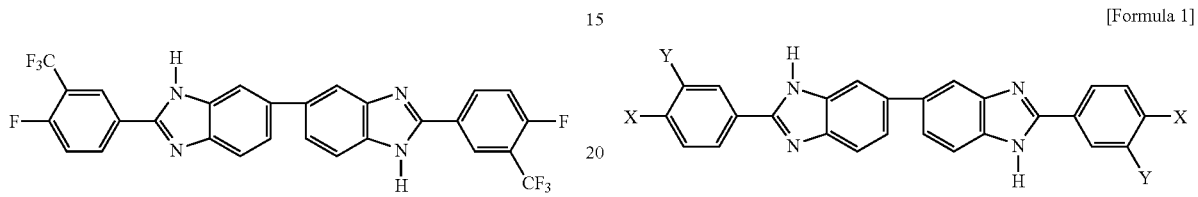

wherein,

X is F, Cl, Br or I and Y is trifluoromethyl ($-CF_3$).

2. The benzimidazole compound as set forth in claim 1, wherein the X is F.

3. The benzimidazole compound as set forth in claim 1, wherein the X is Cl.

4. A benzimidazole polymer synthesized by using the benzimidazole compound of claim 1 as a monomer.

* * * * *